United States Patent
Husheer et al.

(10) Patent No.: US 12,257,073 B2
(45) Date of Patent: Mar. 25, 2025

(54) SYSTEM AND METHOD FOR IDENTIFYING FLUID RETENTION IN A BODY PART

(71) Applicant: Heartfelt Technologies Ltd., Cambridge (GB)

(72) Inventors: Shamus Louis Godfrey Husheer, Borehamwood (GB); Oriane Elisabeth Chausiaux, Cambridge (GB); Gareth Paul Williams, Cambridge (GB)

(73) Assignee: HEARTFELT TECHNOLOGIES LTD., Cambridge (GB)

( * ) Notice: Subject to any disclaimer, the term of this patent is extended or adjusted under 35 U.S.C. 154(b) by 520 days.

(21) Appl. No.: 17/271,604

(22) PCT Filed: Aug. 29, 2019

(86) PCT No.: PCT/IB2019/057279
§ 371 (c)(1),
(2) Date: Feb. 26, 2021

(87) PCT Pub. No.: WO2020/044277
PCT Pub. Date: Mar. 5, 2020

(65) Prior Publication Data
US 2021/0393199 A1    Dec. 23, 2021

(30) Foreign Application Priority Data
Aug. 31, 2018    (GB) .................... 1814230

(51) Int. Cl.
*A61B 5/00* (2006.01)
*G06T 7/00* (2017.01)
*G06T 7/62* (2017.01)

(52) U.S. Cl.
CPC .......... *A61B 5/4878* (2013.01); *G06T 7/0012* (2013.01); *G06T 7/62* (2017.01); *G06T 2207/20036* (2013.01)

(58) Field of Classification Search
CPC .................... G06T 7/62; G06T 15/00
See application file for complete search history.

(56) References Cited

U.S. PATENT DOCUMENTS

| | | | |
|---|---|---|---|
| 10,573,004 B2 | 2/2020 | Husheer | |
| 2006/0062448 A1* | 3/2006 | Hirsch | A61B 5/0062 382/154 |

(Continued)

OTHER PUBLICATIONS

International Search Report, dated Nov. 21, 2019.
Office Action for Mexican Patent Application MX/a/2021/002369, mailed on Oct. 16, 2024, 10 pages.

*Primary Examiner* — Wen W Huang
(74) *Attorney, Agent, or Firm* — FRESH IP PLC; Clifford D. Hyra; Aubrey Y. Chen

(57) ABSTRACT

A method of identifying fluid retention in a body part of the patient by directly or indirectly measuring a first parameter relating to a size of a body part of the patient to obtain an actual measurement of the body part, obtaining an estimated measurement of said first parameter relating to the size of the body part of the patient by measuring alternative predefined parameters of the patient, wherein said estimated measurement is calculated based on a mathematical relationship between said alternative parameters and the size of the body part; and correlating the actual and estimated measurements of the body part of the patient to assess any fluid retention in the body part.

23 Claims, 2 Drawing Sheets

(56) References Cited

U.S. PATENT DOCUMENTS

| | | | |
|---|---|---|---|
| 2011/0208084 A1* | 8/2011 | Seoane Martinez | A61B 5/053 600/547 |
| 2013/0226528 A1* | 8/2013 | Hodgins | B33Y 50/00 703/1 |
| 2014/0249384 A1* | 9/2014 | Levin | A61B 8/0891 600/300 |
| 2015/0046183 A1* | 2/2015 | Cireddu | G16H 10/60 705/3 |
| 2015/0262405 A1* | 9/2015 | Black | G06T 13/40 345/420 |
| 2016/0015297 A1* | 1/2016 | Strauss | A61B 5/4878 600/587 |
| 2016/0100752 A1* | 4/2016 | McHugh | A61B 5/7275 351/205 |
| 2016/0155238 A1* | 6/2016 | Bachschmidt | A61B 5/0037 382/131 |
| 2017/0272728 A1* | 9/2017 | Rafii | G06Q 30/0631 |
| 2018/0206759 A1* | 7/2018 | Ward | A61B 5/4881 |
| 2018/0235539 A1* | 8/2018 | Abdolahi | G16H 50/20 |
| 2018/0240238 A1* | 8/2018 | Husheer | G06V 40/10 |
| 2019/0357776 A1* | 11/2019 | Carreon | A61B 5/02055 |

\* cited by examiner

SYSTEM AND METHOD FOR IDENTIFYING FLUID RETENTION IN A BODY PART

The present invention relates to a system and method for identifying fluid retention in a body part, such as a foot.

TECHNICAL FIELD

Edema (or oedema) is a symptom of importance in many diseases, wherein a part of the body retains excess fluid. This is important in many diseases, such as heart failure (where peripheral edema or foot swelling is observed in over half of hospitalisations) and cancer (where lymphedema is often a complication of cancer treatment).

The most common method for measuring edema is to observe "pitting", wherein the thumb is pressed onto the affected region for a few seconds and then removed, with the resulting indentation or "pit" filling slowly if edema is present as internal tissue fluid slowly fills the "pit". The difficulty with this method is that a quantitative measurement is not possible, due to the local nature of the test and difficulty in grading the depth of pit and speed of refilling.

Other commonly used methods are measurement of circumference or volume of the affected area, and tracking this over time. Whilst these approaches provide a quantitative measure, unless a baseline is known for this particular patient it is challenging to quantify the impact of edema to a single measurement, particularly in the case of obese patients. In cases of unilateral edema, common in lymphedema, it is possible to compare measurements of the affected limb to the opposing limb (e.g. left foot vs right foot), in which case the difference in volumes (or circumference) is both quantitative and specific to the edema itself.

It is an aim of the present invention to provide an improved system and method for identifying fluid retention in a body part, such as foot, which may be indicative of edema associated with multiple diseases.

SUMMARY OF THE INVENTION

To this end, a first aspect of the present invention provide a method of identifying fluid retention in a body part of the patient, the method comprising:
  directly or indirectly measuring a first parameter relating to a size of a body part of the patient to obtain an actual measurement of the body part;
  obtaining an estimated measurement of said first parameter relating to the size of the body part of the patient by measuring alternative predefined parameters of the patient wherein said estimated measurement is calculated based on a mathematical relationship between said alternative parameters and the size of the body part; and
  correlating the actual and estimated measurements of the body part of the patient to assess any fluid retention in the body part.

Preferably, the step of measuring the first parameter comprises directly or indirectly measuring a volume of, a thickness of, or a circumference of the body part, more preferably comprising imaging of the body part to obtain a volume of, a thickness of, or a circumference of the body part.

In a preferred embodiment of the invention, said imaging of the body part includes three-dimensional imaging of the body part to yield the measurement of the first parameter, preferably associating the three-dimensional data with a three-dimensional model of the body part.

The method may further comprise extracting both sets of measurements substantially simultaneously using a mathematical modelling system to provide an actual model and an estimated model based on population-derived model parameters and comparing the models to determine whether the actual model identifies fluid retention in the body part. The first volume may be obtained by providing a first deformable model with multiple morph parameters based on the actual body part and comparing this with a second model based on pre-defined parameters and fluid retention, such as a second model with multiple morph parameters, the second model being based on predefined parameters representing population-derived values without any fluid retention or with a known amount of fluid retention, thereby enabling the general structure of the patient to be well modelled whilst estimating the fluid-retention free shape of the body part and optionally calculating the difference between the first and estimated volumes to assess any fluid retention in the body part of the patient.

According to the invention, the step of measuring the first parameter may comprise directly or indirectly measuring a volume of the body part.

The step of estimating the first parameter may comprise directly or indirectly measuring a volume of the body part by measuring multiple other parameters of the body part to calculate the volume of the body part based on these measurements. Preferably, the estimated measurement comprises an estimated volume of the body part based on measuring alternative predefined parameters correlating to the volume of the body part, said estimated volume being calculated based on a mathematical relationship between said alternative parameters and the body part. The estimated volume is preferably calculated based on measurements selected from one or more of a length of the body part, a width of the body part, a weight of the body part, a height of the body part, a density of the body part and a circumference of the body part. Said estimated volume may be adjusted in accordance with an overall patient height, weight and/or bioimpedance.

The method according to the invention may comprise obtaining and processing the measurements at intervals over time to track changes in fluid retention in a patient. The method may be computer-implemented and further comprise assessing and/or communicating the patient's health status and risk based on an identified difference between the actual and estimated measurements of the body part.

Preferably, the body part is a foot.

According to a second aspect of the present invention there is provided a system for identifying fluid retention in a body part of the patient, the system comprising:
  a measuring instrument to directly or indirectly measure a first parameter relating to a size of a body part of the patient, the measuring instrument providing an actual measurement of the body part;
  a measurement data comparison unit configured to compare the actual measurement of the body part with an estimated measurement for said parameter of the body part, wherein the estimated measurement is based on measuring alternative parameters of the patient and calculated based on a mathematical relationship between said alternative parameters; and
  a diagnostic unit configured to determine fluid retention in the body part of the patient based on a result of comparing by the comparison unit.

The measuring instrument preferably comprises a depth sensing camera apparatus. The depth sensing camera apparatus may comprise at least one emitter and one detector array, or at least two detector arrays.

DETAILED DESCRIPTION

In the course of evaluating the clinical effectiveness of our 3D limb volume measurement system described in the inventor's co-pending application (GB2542114B), the inventor has surprisingly found that it is possible to gain a remarkably quantitative single measurement of fluid retention indicative of edema in a limb by the difference in two volumes.

The first volume is that observed most directly from the patient's body part of interest (e.g. by 3D imaging, or water displacement, or estimation of cylindrical segment volumes from multiple circumference measurements, or any other method known in the art). The second volume is that calculated based on a mathematical relationship between certain measured parameters on the patient (e.g. patient height, weight, and bone lengths) and resulting in an estimate of the volume of the body part of interest, wherein the mathematical relationship provides an estimate that is related to a more general patient population, ideally without edema but with sufficient variation in confounding factors such as variation in body fat.

A simple example for the first volume measurement is to measure the volume, in millilitres, of the patient's foot up to a height of 20 cm from the ground, by water displacement when the patient stands in a filled bucket of water. This provides an accurate (though not easy to administer) measurement of the total foot volume.

A simple example for the second volume measurement is to relate the volume of the foot up to a height of 20 cm to the length of the foot, as measured from tip-of-big-toe to back-of-heel, where the volume estimate in millilitres is 60 times the foot-length in centimetres.

The difference of these two measurements, volume one minus volume two, gives a number which is surprisingly effective in classifying patients in a heart failure population into those who were determined by a clinician at an outpatient appointment as having pitting edema present, and those who did not. Over 80% of patients clinically assessed as having pitting edema had a positive volume difference by this measure, whilst over 80% of patients clinically assessed as not having pitting edema, or presenting as healthy volunteers, had a negative volume differences by this measure. Moreover, the magnitude of this difference correlated well with the subjective clinical grading of degree of edema in patients.

Figure 1:
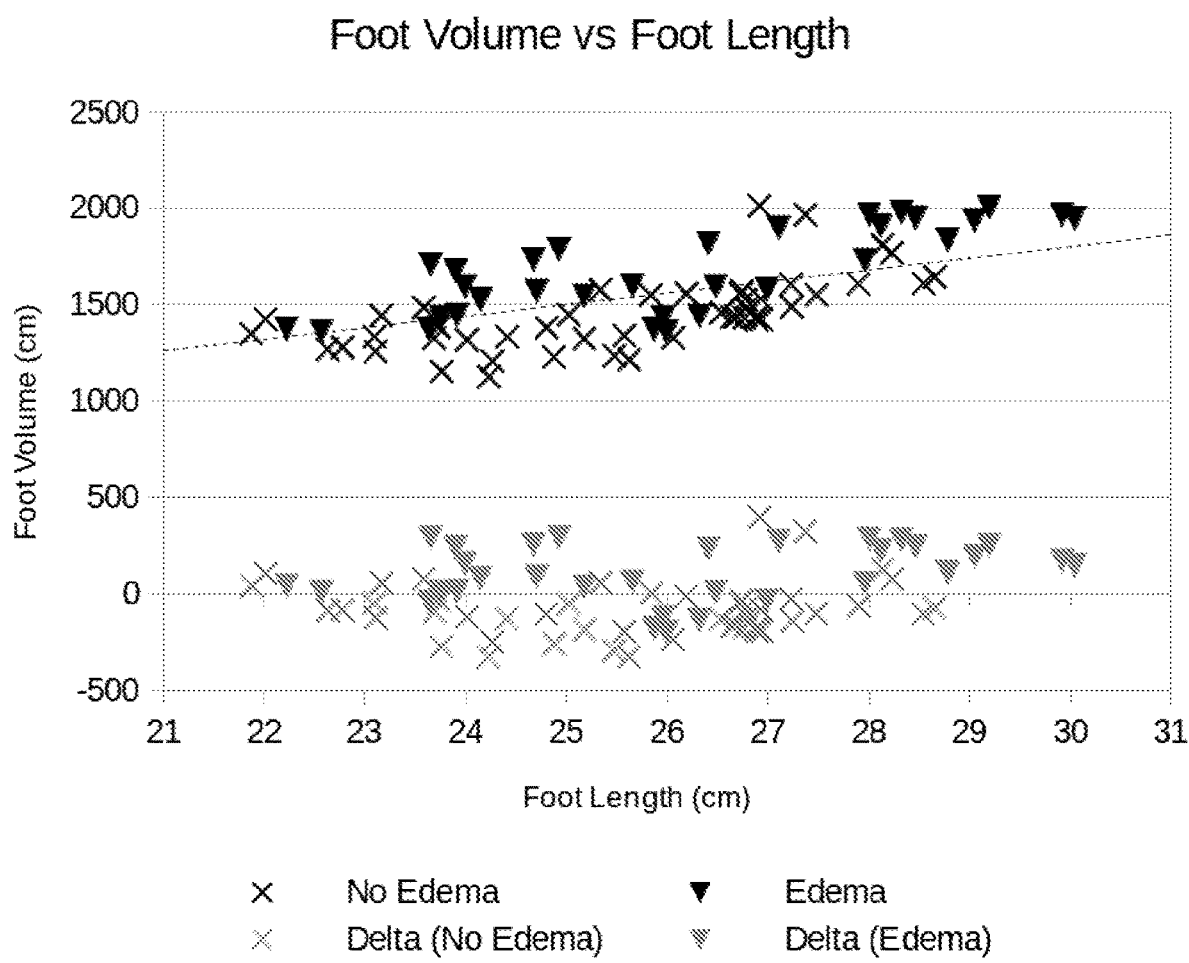
FIG. 1 is a graph illustrating foot volume against foot length for a patient with edema and a patient without edema.

FIG. 1 displays a chart of the foot lengths and foot volumes split by clinician assessment of edema status.

Naturally a relationship based only on foot-length will be subject to error resulting from body fat percentage. More complex models including e.g. patient height and weight or bioimpedance will naturally provide better correlation with edema in the presence of e.g. body fat as a confounding factor.

An alternative, preferred approach is to use a single mathematical modelling system to extract both sets of volumes at once. For example, when using a 3D camera system it is generally possible to fit a deformable model to the observed 3D points collected from the camera. The objective is generally to allow certain model parameters, such as bone joint angles and lengths, to adjust in order to minimize the difference between points on the virtual model surface and the observed 3D points. Such a model also typically includes parameters that adjust the shape of the model, often called "morphs" in the 3D rendering community, which might for example alter the volume of flesh around the virtual bones and allow the volume of flesh to be scaled over a range of numerical values.

In building and testing such a model on the same heart failure patient population, it was found that certain of these "morphs" were very much more strongly correlated to subjective clinical grading of edema than others. For example, volume changes around the ankle that essentially flatten out the malleolus of the foot were found to correlate more strongly with clinical grading of edema than with patient BMI.

Figure 2:
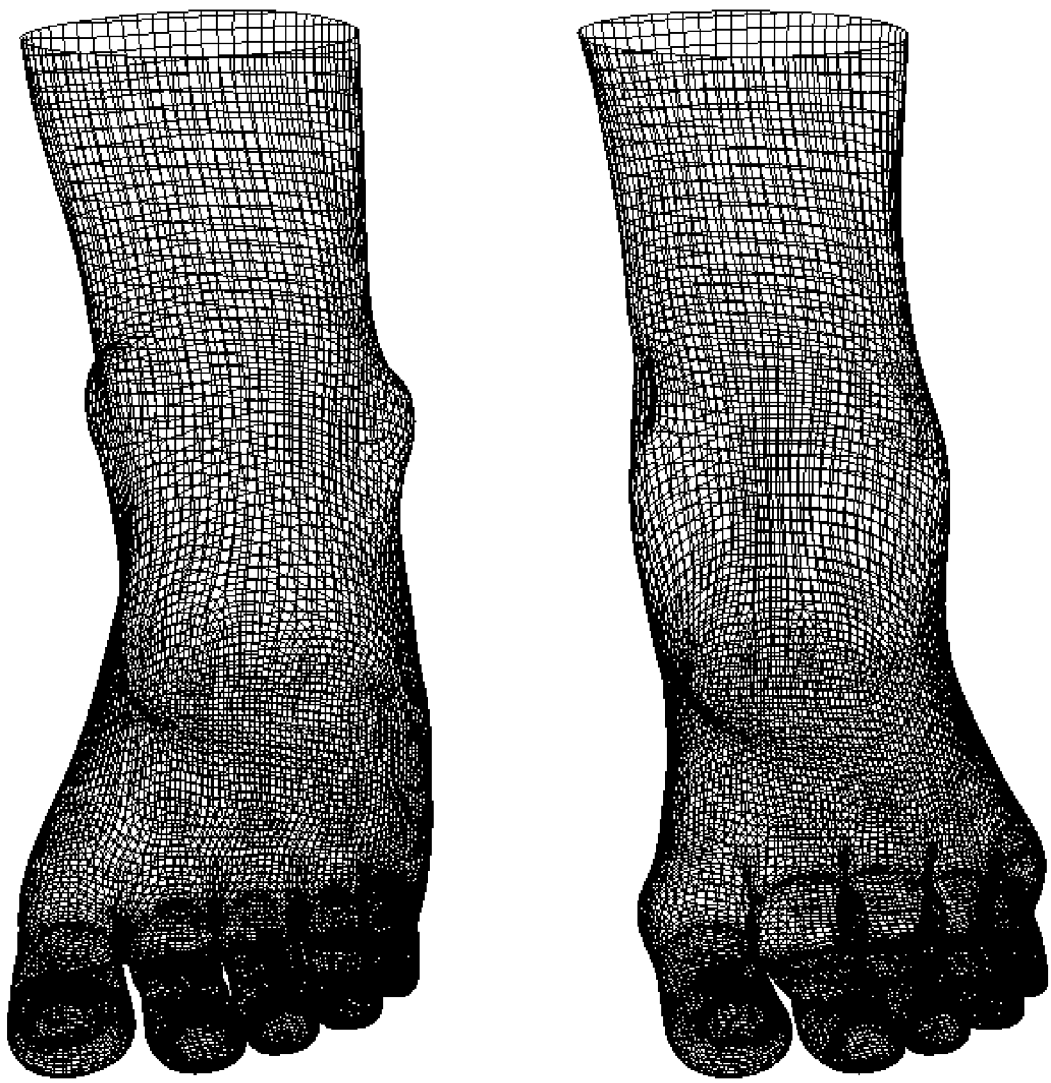
FIG. 2 is a foot model created by 3D imaging of a foot without edema-specific morphs (shown on the left of the figure) and with edema specific morphs (shown on the right of the figure) for a patient.

FIG. 2 displays such three dimensional foot model, on the left without the application of edema-specific "morphs", and on the right with the application of these morphs, for a particular patient. The additional mass around the malleolus bone is particularly obvious in the right model.

Furthermore, a number of patients in the heart failure trial were monitored whilst undergoing a course of diuretic therapy, with the aim of reducing fluid retention and thus edema. It was therefore possible to observe which "morphs" correlated with change in foot volume over time for a particular patient, which implies a direct correlation to fluid retention indicative of edema.

An approach to edema estimation was therefore enabled whereby the observed 3D foot data was modelled using the deformable model, with all morph parameters being allowed to vary freely, in order to provide the first volume. The second volume was then calculated by resetting the values of those morphs that were found to correlate with edema to population average values. This enables the general structure of the foot for this particular patient to be well modelled, whilst estimating the edema-free shape of the foot. The difference between the two volumes calculated by this technique was found to be particularly sensitive to changes in edema over time in the patients underdoing diuretic treatment, and also correlated well with the subjective clinical evaluation of edema.

The difference between the two volumes can obviously be processed further to provide various useful indicators. For example, by expressing the percentage of patients with and without clinician-determined edema who exhibit more or less than various threshold volume differences, it is possible to estimate the probability that a patient exhibiting a particular volume difference would be assessed as having edema by a clinician. This is useful for risk-scoring and risk-stratification of patients, especially when combined with other clinical indicators that are also probabilistic in nature.

This invention is not only useful in the clinic, in providing a numerical measure of fluid retention indicative of edema, but if implemented using suitable methods (such as 3D cameras) could provide a measure of a change in fluid retention from the patient's home. This could not only save on transport to hospital appointments for the patient or to the patient by the clinical team, but if implemented as part of a telemedicine system could provide alerts of worsening patient health. Such a system might plausibly reduce the presently very high repeat hospitalisation rates for chronic conditions such as heart failure, not only saving substantial healthcare resources but providing better quality of life for patients.

It will be obvious that a "difference" between volumes need not be a simple subtractive difference, but could also be ratiometric, or the result of any number of statistical tests or other numerical comparison.

It will also be apparent that a multitude of volumetrically related model outputs could be used in embodiments of the invention as opposed to strictly using volume. For example, the aforementioned virtual 3D model could have the thickness or circumference virtually measured at various locations, and these virtual circumference measurements compared, or the surface-area of 3D models could be compared. For the purposes of this invention, all of these types of comparison are to be considered as a non-limiting list of possible size comparisons within the meaning of the claims.

The invention claimed is:

1. A method of identifying fluid retention in a body part of the patient, the method comprising:
    measuring, from three-dimensional imaging of a body part of the patient, a first body parameter indicative of a size of the body part to obtain an actual measurement of the body part, wherein the three-dimensional imaging yields the actual measurement of the first body parameter and provides a first deformable model with a first set of morph parameters based on the body part;
    obtaining an estimated measurement of the first body parameter indicative of the size of the body part of the patient, wherein the obtaining the estimated measurement of the first body parameter comprises measuring a second body parameter of the body part of the patient that is correlated with the first body parameter; and
    correlating the actual and estimated measurements of the first body parameter of the patient to assess any fluid retention in the body part;
    wherein the correlating further comprises comparing the first deformable model with the estimated measurement.

2. A method according to claim 1, further comprising associating the three-dimensional data with a three-dimensional model of the body part.

3. A method according to claim 1, wherein the second parameter is selected from the group consisting of: a length of the body part, a width of the body part, a weight of the body part, a height of the body part, a density of the body part, a circumference of the body part, and combinations thereof.

4. A method according to claim 1, wherein the obtaining the estimated measurement of the first body parameter further comprises calculating, based on the measurement of the second body parameter, an estimate of a volume of the body part of the patient.

5. A method according to claim 1, wherein at least one morph parameter in the first set of morph parameters is correlated with edema in the body part.

6. A method according to claim 1, wherein the estimated measurement is adjusted in accordance with the patient's height, weight and/or bioimpedance.

7. A method according to claim 1, further comprising obtaining and processing the measurements at intervals over time to track changes in fluid retention in the patient.

8. A method according to claim 1, wherein the body part is a foot.

9. A method according to claim 1, wherein the method is computer-implemented and further comprises assessing and/or communicating the patient's health status and risk based on an identified difference between the actual and estimated measurements of the body part.

10. A method according to claim 1, further comprising: estimating a fluid retention-free shape of the body part.

11. A method according to claim 10, wherein the correlating the actual and estimated measurements of the body part of the patient further comprises:
    calculating a difference between the actual measurement and the estimated measurement;
    estimating a probability, based on the difference, that the patient would be classified as having edema.

12. A method according to claim 1, wherein the fluid retention comprises edema.

13. A system for identifying fluid retention in a body part of the patient, the system comprising:
    a measuring instrument comprising a depth sensing camera apparatus to provide a three-dimensional imaging of the body part and associating three-dimensional data with a three-dimensional model of the body part to yield an actual measurement of a first body parameter indicative of a size of the body part;
    a measurement data comparison unit configured to compare the actual measurement of the body part with an estimated measurement for the first body parameter of the body part, wherein the estimated measurement is obtained by measuring a second body parameter of the body part that is correlated with the first body parameter; and
    a diagnostic unit configured to determine fluid retention in the body part of the patient based on a result of comparing the actual and estimated measurements by the comparison unit.

14. A system as claimed in claim 13, wherein the depth sensing camera apparatus comprises at least one emitter and one detector array, or at least two detector arrays.

15. A system as claimed in claim 13, wherein the measuring instrument is configured to provide a first deformable model with a first set of morph parameters based on a volume of the actual body part from the three-dimensional imaging for the first body parameter.

16. A system as claimed in claim 15, wherein the first set of morph parameters comprise one or more volume changes around an ankle of the patient that result in a flattening of a malleolus of a foot of the patient.

17. A system as claimed in claim 13, wherein the measuring data comparison unit is configured to provide the estimated measurement.

18. A system as claimed in claim 13, wherein the estimated measurement is adjusted in accordance with the patient's body fat percentage.

19. A method of identifying fluid retention in a body part of the patient, the method comprising:
    measuring an actual volume of a body part of a patient by three-dimensional (3D) imaging of the body part;
    measuring one or more body parameters correlated to a volume of the body part to calculate an estimated volume of the body part wherein the estimated volume is based on a mathematical relationship between the one or more body parameters and the actual volume;
    adjusting the estimated volume based on the patient's height, weight, and/or bioimpedance;
    extracting, by a mathematical modeling system, the actual volume and the estimated volume to provide an actual model and an estimated model;

comparing the actual model and the estimated model to determine whether the actual model identifies fluid retention in the body part,
wherein the mathematical relationship is based on a general patient population that (i) has variation in body fat percentages, and (ii) does not have any fluid retention.

20. A method according to claim 19, further comprising:
fitting a deformable model to a plurality of points on the actual model;
wherein the deformable model comprises a set of measurable parameters of the body part and a plurality of morphs,
wherein the set of measurable parameters are adjustable in order to minimize a difference between the plurality of points on the actual model and a plurality of points on the estimated model,
wherein the plurality of morphs adjust a shape of the actual model.

21. A method according to claim 20, wherein the body part is a foot, wherein the set of measurable parameters comprises at least one of: a bone joint angle and a bone length, and wherein the plurality of morphs comprises one or more volume changes around an ankle of the patient.

22. A method according to claim 20, wherein the plurality of morphs comprises at least one morph that is correlated with fluid retention of the body part.

23. A method according to claim 20, wherein at least one morph alters a volume of flesh around one or more bones of the body part.

* * * * *